US009259516B2

(12) United States Patent
Bayer

(10) Patent No.: US 9,259,516 B2
(45) Date of Patent: Feb. 16, 2016

(54) IMPLANT AND METHOD FOR MANUFACTURING

(75) Inventor: Ullrich Bayer, Admannshagen-Bargeshagen (DE)

(73) Assignee: Biotronik VI Patent AG, Baar (CH)

(*) Notice: Subject to any disclaimer, the term of this patent is extended or adjusted under 35 U.S.C. 154(b) by 350 days.

(21) Appl. No.: 12/576,050

(22) Filed: Oct. 8, 2009

(65) Prior Publication Data

US 2010/0161053 A1    Jun. 24, 2010

(30) Foreign Application Priority Data

Dec. 18, 2008 (DE) .................. 10 2008 054 920

(51) Int. Cl.
*A61F 2/02* (2006.01)
*A61L 31/14* (2006.01)
*A61L 31/02* (2006.01)
*A61L 31/08* (2006.01)

(52) U.S. Cl.
CPC .............. *A61L 31/148* (2013.01); *A61L 31/022* (2013.01); *A61L 31/028* (2013.01); *A61L 31/088* (2013.01)

(58) Field of Classification Search
CPC ............ A61F 2/06; A61L 31/10; A61L 31/16
USPC .................... 623/23.55, 1.46, 1.38, 1.44
See application file for complete search history.

(56) References Cited

U.S. PATENT DOCUMENTS

| | | | |
|---|---|---|---|
| 5,383,935 A * | 1/1995 | Shirkhanzadeh | 623/23.49 |
| 5,873,904 A * | 2/1999 | Ragheb et al. | 623/1.13 |
| 6,355,058 B1 * | 3/2002 | Pacetti et al. | 623/1.15 |
| 6,716,444 B1 | 4/2004 | Castro et al. | |
| 6,790,228 B2 * | 9/2004 | Hossainy et al. | 623/1.46 |
| 7,985,252 B2 * | 7/2011 | Radhakrishnan et al. | 623/1.46 |
| 8,388,678 B2 * | 3/2013 | Singhal et al. | 623/1.42 |
| 8,992,596 B2 * | 3/2015 | Bayer et al. | 623/1.15 |
| 2004/0254604 A1 | 12/2004 | Viart et al. | |
| 2005/0019365 A1 * | 1/2005 | Frauchiger et al. | 424/423 |
| 2006/0121080 A1 * | 6/2006 | Lye et al. | 424/423 |
| 2006/0222679 A1 * | 10/2006 | Shanley et al. | 424/423 |
| 2007/0207186 A1 * | 9/2007 | Scanlon et al. | 424/424 |
| 2007/0237946 A1 | 10/2007 | Ohrlander et al. | |
| 2008/0243242 A1 | 10/2008 | Kappelt et al. | |
| 2009/0024205 A1 * | 1/2009 | Hebert et al. | 623/1.16 |
| 2010/0070022 A1 * | 3/2010 | Kuehling | 623/1.16 |
| 2010/0087916 A1 * | 4/2010 | Bayer et al. | 623/1.46 |
| 2010/0262221 A1 * | 10/2010 | Schafer et al. | 623/1.13 |
| 2010/0316686 A1 * | 12/2010 | Dingeldein et al. | 424/422 |

FOREIGN PATENT DOCUMENTS

| | | |
|---|---|---|
| DE | 100 44 559 A1 | 4/2002 |
| DE | 202005006181 U1 | 4/2005 |
| DE | 60302447 T2 | 7/2006 |
| DE | 102006060501 A1 | 6/2008 |
| DE | 10 2007 004 589 A1 | 7/2008 |
| EP | 1 494 729 B3 | 6/2009 |
| EP | 2172234 A2 | 4/2010 |
| WO | WO 01/41829 A1 | 6/2001 |
| WO | WO 01/49340 A1 | 7/2001 |
| WO | 0220062 A2 | 3/2002 |
| WO | 2008092436 A2 | 8/2008 |

* cited by examiner

*Primary Examiner* — Paul Prebilic
(74) *Attorney, Agent, or Firm* — Wagenknecht IP Law Group PC

(57) ABSTRACT

The present invention proposes an implant, in particular an intraluminal endoprothesis, having a body, comprising at least one at least largely biodegradable metallic material, in particular magnesium or a magnesium alloy. To improve the degradation behavior, the implant has a first layer on at least a portion of its body surface, said layer containing a hydrogen-binding material, preferably palladium. Furthermore, methods for producing such an implant are given.

10 Claims, No Drawings

IMPLANT AND METHOD FOR MANUFACTURING

CROSS REFERENCE TO RELATED APPLICATIONS

This invention claims benefit of priority to Germany patent application serial number DE 10 2008 054 920.7, filed on Dec. 18, 2008; the contents of which are herein incorporated by reference in their entirety.

FIELD OF THE INVENTION

The invention relates to an implant, in particular an intraluminal endoprosthesis, and a method for manufacturing this implant.

BACKGROUND OF THE INVENTION

Medical endoprostheses or implants for a wide variety of applications are known in a great variety from the prior art. Endoprostheses in the sense of the present invention are understood to be endovascular prostheses, e.g., stents, fastening elements for bones, e.g., screws, plates or nails, surgical suture material, intestinal clamps, vascular clips, prostheses in the area of hard and soft tissue as well as anchoring elements for electrodes, in particular pacemakers or defibrillators.

Stents are used today as implants in especially large numbers to treat stenoses (vasoconstrictions). They have a tubular basic mesh or hollow cylinder, which is open at both longitudinal ends. The tubular basic mesh of such an endoprosthesis is inserted into the vessel to be treated and serves to support the vessel there. Stents have become established for treatment of vascular diseases in particular. Constricted regions in the vessels can be widened through the use of stents, resulting in a larger lumen. Through the use of stents or other implants, an optimum vascular cross section, which is the first requirement for successful treatment, can be achieved, but the permanent presence of such a foreign body initiates a cascade of microbiological processes, which can lead to gradual overgrowth of the stent and, in the worst case, to vascular occlusion. One approach to solving this problem is to manufacture the stent and/or other implants from a biodegradable material.

"Biodegradation" is understood to refer to hydrolytic, enzymatic and other metabolic degradation processes in a living body, where these processes are triggered mainly by body fluids coming in contact with the biodegradable material of the implant and lead to a gradual dissolution of the structures of the implant containing the biodegradable material. Through this process, the implant loses its mechanical integrity at a certain point in time. The term "biocorrosion" is often used as synonymous with "biodegradation." The term "bioresorption" comprises the subsequent resorption of the degradation products by a living body.

Materials suitable for the basic mesh of biodegradable implants may contain polymers or metals, for example. The basic mesh may consist of several of these materials. The common feature shared by all these materials is their biodegradability. Examples of suitable polymer compounds include polymers from the group of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), poly/alkyl carbonates, polyorthoesters, polyethylene terephthalate (PET), polymalonic acid (PML), polyanhydrides, polyphosphazenes, polyamino acids and their copolymers as well as hyaluronic acid. Depending on the desired properties, the polymers may be used in pure form, in derivatized form, in the form of blends or copolymers. Metallic biodegradable materials are based primarily on alloys of magnesium and iron. The present invention preferably relates to implants whose biodegradable material contains at least partially a metal, preferably magnesium or a magnesium alloy.

There are already known stents which have coatings with various functions. Such coatings serve, for example, to release medications, to arrange an X-ray marker or to protect the underlying structures.

In the implementation of biodegradable implants, the degradability should be controlled according to the desired treatment and/or application of the respective implant (coronary, intracranial, renal, etc.). For many therapeutic applications, for example, an important target corridor is for the implant to lose its integrity over a period of four weeks to six months. The term "integrity" here is understood to be mechanical integrity, i.e., the property whereby the implant has hardly any mechanical losses in comparison with the undegraded implant. This means that the implant has such high mechanical stability that the collapse pressure, for example, drops only slightly, i.e., at most to 80% of the nominal value. Thus if it has its integrity, the implant can fulfill its main function, to maintain the patency of the blood vessel. Alternatively, integrity may be defined as such a great mechanical stability of an implant that it is hardly subject to any geometric changes in its load state in the vessel, e.g., it does not collapse to any mentionable extent, i.e., it still has at least 80% of the dilated diameter under load or, in the case of a stent, there are hardly any broken load-bearing struts.

Biodegradable implants containing magnesium or a magnesium alloy, in particular so-called magnesium stents, have proven to be especially promising for the target corridor of degradation mentioned above, but they lose their mechanical integrity and/or supporting effect too soon on the one hand, while on the other hand, the decline in integrity varies greatly in vitro and in vivo. This means that with magnesium stents, the collapse pressure declines too rapidly over time and/or there is too much variability in this decline so it is too indefinable.

Various mechanisms of controlling the degradation of magnesium implants have already been described in the prior art. These are based on organic and inorganic protective layers, for example, or combinations thereof, which present some resistance to the human corrosion medium and the corrosion processes taking place there. Approaches known in the past have been characterized in that barrier layer effects are achieved, based on the best spatial separation between the corrosion medium and the metallic material, in particular the metallic magnesium, with no defects, if possible. Protection from degradation is thus ensured by protective layers having various compositions and by defined geometric spacings (diffusion barriers) between the corrosion medium and the magnesium base material. Other approaches are based on alloy constituents of the biodegradable material of the implant body, which influence the corrosion process by shifting its position in the electrochemical voltage series. Other approaches in the field of controlled degradation produce intended breaking effects by applying physical changes (e.g., local changes in cross section) and/or chemical changes to the stent surface (e.g., multiple layers having different chemical compositions locally). However, with the approaches mentioned so far, it has not usually been possible to arrange for the dissolution, which occurs due to the degradation process, and the resulting breakage of the webs to occur within the required window of time. The result is that degradation occurs either too soon or too late and/or there is excessive variability in the degradation of the implant.

Another problem associated with passivation coatings is based on the fact that stents or other implants may usually assume two states, namely a compressed state with a small diameter and an expanded state with a larger diameter. In the compressed state, the implant can be inserted by means of a catheter into the vessel to be supported and positioned at the location to be treated. At the site of treatment, the implant is then dilated by means of a balloon catheter and/or converted to the expanded state (when a shape memory alloy is used as the implant material) by heating it to a temperature above the transition temperature. Because of this change in diameter, the implant body is subjected to mechanical stress. Additional mechanical stresses on the implant may occur during production or movement of the implant in or with the blood vessel into which the implant has been inserted. With the aforementioned coatings, this yields in particular the disadvantage that the coating may crack during deformation of the implant (e.g., forming microcracks) or may be partially removed. This may cause an unspecified local degradation. Furthermore, the onset and rate of degradation depend on the size and distribution of the microcracks formed during deformation, which, being defects, are difficult to control. This leads to a great scattering in the degradation times.

Document DE 10 2006 060 501 discloses a method of manufacturing a corrosion-inhibiting coating on an implant made of a biocorrodible magnesium alloy and an implant obtainable by this method, in which, after the implant is prepared, the implant surface is treated with an aqueous or alcoholic conversion solution containing one or more ions selected from the group of $K^-$, $Na^+$, $NH_4^+$, $Ca^{2+}$, $Mg^{2+}$, $Zn^{2+}$, $Ti^{4-}$, $Zr^{4+}$, $Ce^{3+}$, $Ce^{4+}$, $PO_3^{3-}$, $PO_4^{3-}$, $HPO_4^{2-}$, $H_2PO_4^-$, $OH^-$, $BO_3^{3-}$, $B_4O_7^{3-}$, $SiO_3^{2-}$, $MnO_4^{2-}$, $MnO_4^-$, $VO_3^-$, $WO_4^{2-}$, $MoO_4^{2-}$, $TiO_3^{2-}$, $Se^{2-}$, $ZrO_3^{2-}$ and $NbO_4^-$, where the concentration of the ion(s) is in the range of $10^{-2}$ mol/L to 2 mol/L. The treatment of the implant surface with said conversion solution causes anodic oxidation of the implant. This is performed either without the use of an external current source (externally currentless) or with a current source. However, neither the examples of methods described in this publication nor the electrolyte compositions completely meet expectations with regard to degradation behavior and dilatability without destruction of the layer being used for a magnesium stent.

BRIEF SUMMARY OF THE INVENTION

The object of the present invention is thus to provide a method for manufacturing a degradation-inhibiting layer structure on an implant body, which facilitates degradation of the implant in the desired target corridor. The degradation should occur at a controllable point in time and should additionally facilitate dilatation and/or deformation of the implant without having any mentionable influence on the degradation behavior. Accordingly, the object of the invention is to create such an implant.

The above object is achieved by an implant having a first layer which contains a hydrogen-binding material, preferably palladium, on at least a portion of its body surface. The reference to binding of hydrogen here is understood to include binding of hydrogen in the lattice of the hydrogen-binding material as well as the formation of hydrides. The implant body comprises at least a portion of the implant, preferably most of the implant which is responsible for the mechanical integrity of the implant.

DETAILED DESCRIPTION OF THE INVENTION

The present invention is based on the finding that in particular when using magnesium or magnesium alloys for implants in contact with endogenous fluids, degradation phenomena are associated with the release of hydrogen as a reaction product. The hydrogen leads to an extreme local reduction in pH and, associated with this, increased corrosion. It has been found that hydrogen cannot be prevented from forming when magnesium alloys come in contact with aqueous media, but improved degradation behavior can be achieved by the fact that the hydrogen is bound in a positive or integrally bonded manner over long periods of time directly at its site of formation, i.e., at the surface of the implant. Its influence on the corrosion rate can be reduced significantly in this way.

The traditional approach has therefore consisted of slowing down the corrosion rate of magnesium implants by applying various protective layers. The main emphasis here has been placed on achieving a physical separation between the magnesium material and the electrolyte/body fluid such that it would have the greatest possible long-term stability. Examples include conversion layers on the basis of magnesium fluoride, deposition layers with titanium, SiC, magnesium, magnesium oxide applied in various ways or anodically created mixed compounds of magnesium oxide and magnesium phosphate. More extensive approaches have also been based on the assumption that calcium phosphate, the dominant reaction product on the surface of the body is applied in advance and the reaction rate of the corrosion process is thereby retarded. One disadvantage of the known approaches is that they have only a low failure tolerance. If these layers are damaged by mechanical influences or by corrosive attack and then the magnesium base material subsequently comes in direct chemical contact with the electrolyte/body fluid, locally unrestrained corrosion occurs. The resulting hydrogen ions diffuse partially into the surface of the magnesium and embrittle it, while another portion recombines to form molecular hydrogen and create bubbles, which adhere to the magnesium surface. These bubbles grow and are separated from the surface due to the turbulence of the electrolyte (blood, plasma, etc.). The geometry of the implants causes the body fluid flowing by with the frequency of the pulse rate to create turbulence of varying intensities and therefore locally variable shearing effects on the hydrogen bubbles. This has the result that each bubble acts on the implant surface for different periods of time, depending on the position with respect to the implant. The associated differences in reaction times in turn lead to a heterogeneous corrosive attack and, associated with that, a variable conversion of metallic magnesium to magnesium hydroxide. For the case when anticorrosion layers are present (e.g., calcium phosphates, magnesium phosphates, magnesium fluoride or magnesium oxide), there is the risk due to the release of hydrogen in degradation that the hydrogen may migrate under the protective layers. This creates fragments of the implant body, which separate from the implant and are exposed to additional corrosive attacks without any physical connection to the remaining implant. The remaining implant is thus also subject to advancing corrosion. The larger surface area thereby formed has cavities, which further enhance the corrosive attack. This results in formation of fissured residual cross sections and corroded fragments surrounded by neointima. Ultimately the webs of the implant break and there is a complete loss of mechanical integrity of the magnesium component.

The accomplishment of the inventor is to have recognized in an inversion of the known approaches that the damaging effects of hydrogen described here, which are caused by the release of hydrogen as a reaction product in degradation, are prevented or at least minimized by a hydrogen-binding coating, i.e., an absorbent coating.

The efficacy of the palladium particles contained in the first layer as temporary hydrogen storage mechanisms will now be explained on the example of a vascular stent. Nanoscale palladium particles, which are preferred for use, as explained in greater detail below, can store up to a 12,000-fold volume of hydrogen in a body fluid environment. It is also known that in corrosion of 1 mg magnesium in an aqueous medium, hydrogen is released in an amount of approx. 900 $mm^3$. Complete corrosion of a magnesium component with a mass of 4 mg. which is typical for vascular stents, thus releases 3,600 $mm^3$ hydrogen. A palladium layer approx. 5 μm thick on a stent with a surface area of approx. 70 $mm^2$ takes up a volume of approx. 0.35 $mm^3$, so this layer can bind approx. 4.200 $mm^3$ hydrogen (0.35 $mm^3$×12,000). A palladium layer 5 μm thick is thus capable of binding all the hydrogen released by complete degradation of the stent. Even under the assumption that not all of the palladium is converted to palladium hydride, at least large portions of the hydrogen formed by degradation can be chemically bound by a 5-μm-thick layer containing palladium. The palladium acts as a "sacrificial element" in the broadest sense. Due to the bound hydrogen, the corrosive effect of the electrolyte/body fluid surrounding the implant is diminished and the degradation time of the magnesium implant is thereby increased. "Normal" degradation, i.e., degradation with the involvement of hydrogen that is released and is not bound, does not begin until all of the palladium that comes in contact with the electrolyte has been converted to palladium hydride. The resulting palladium hydride initially remains in the vessel, in addition to the implant, which is subject to advancing fragmentation and continues to corrode down to the submicrometer range and to some extent is also incorporated by the surrounding endogenous matrix.

Another advantage of a coating that contains palladium is that palladium has good radiopacity and therefore can also act as an X-ray marker. Even after the palladium has been converted to palladium hydride, it still has good radiopacity because of its high density of approx. 12 $g/cm^3$ and its atomic number of 46 and it can be detected by an X-ray apparatus even after conversion when it remains in the blood vessel in addition to the implant and thus can also be used as an indicator for the degradation of the magnesium component, in particular when using high-density X-ray energy.

In a preferred exemplary embodiment, the concentration of the hydrogen-binding material, in particular the palladium concentration in the first layer is between approx. 90 wt % and approx. 100 wt %. At such a concentration, a large amount of hydrogen can be bound in particular.

The first layer may have a layer thickness of approx. 1 μm to approx. 10 μm, for example, preferably approx. 2 μm to approx. 6 μm. As already explained above on the basis of an example, a sufficient amount of hydrogen can be bound with a layer volume based on the layer thickness of a few micrometers, so that degradation of the degradable implant is significantly delayed.

In another exemplary embodiment, the average particle size of the palladium particles is between approx. 20 nm and approx. 15 μm, preferably between approx. 50 nm and approx. 500 nm. The average particle size here was determined as the arithmetic mean of the measured particles by means of scanning electron microscopic methods. Nanoscale palladium particles in particular are capable of storing many times their volume of hydrogen. Consequently, it is advantageous to select the largest possible particle sizes in the stated range.

In another exemplary embodiment, the implant has a second layer, which is arranged above the first layer on a portion of its body surface, the second layer preferably containing parylene and/or magnesium stearate.

The degradation time of the implant can be increased again significantly by a parylene protective layer, preferred layer thicknesses of the parylene layer being between approx. 0.5 μm and approx. 10 μm. Parylene here is the name for completely linear, partially crystalline and uncrosslinked aromatic polymers. The various polymers have different properties and can be classified in four basic groups, namely parylene C, parylene D, parylene N and parylene F.

A coating that contains magnesium stearate also has an advantageous effect on the properties of the implant. The magnesium stearate coating produces a greater adhesion of the palladium particles to the body surface or to the underlying intermediate layer, in particular when the latter has pores. The magnesium stearate coating preferably has a layer thickness between approx. 0.5 μm and approx. 10 μm.

In another exemplary embodiment, an intermediate layer preferably produced by a plasma chemical treatment is arranged between the surface of the implant body and the first layer, this intermediate layer being porous and being provided on at least a portion of the surface of the implant body, where the thickness of the intermediate layer preferably amounts to approx. 1 μm to approx. 20 μm, especially preferably approx. 2 μm to approx. 8 μm. In an especially preferred exemplary embodiment, the intermediate layer contains at least one compound selected from the group including phosphates, hydroxides and oxides of the biodegradable metallic material or the biodegradable metallic materials of the implant body.

The plasma chemical treatment comprises the treatment in an aqueous electrolyte system (aqueous solution) in which plasma chemical effects occur directly at the surface of the implant body. The plasma is stable for a few microseconds at the surface of the implant body, creating reaction products that lead to development of the intermediate layer on the surface of the implant body. The intermediate layer is preferably arranged on a corresponding portion of the surface area of the implant body or over the entire surface, so that the intermediate layer comes to lie between the surface of the implant body and the first layer, which contains a hydrogen-binding material.

Due to the plasma chemical treatment, phosphates, hydroxides and oxides of the metallic material, in particular magnesium, are formed on the surface of the implant body. This layer composition provides temporary corrosion protection when the implant comes in contact with body fluid and thus delays the degradation of the metallic material. The particles released in the wake of the delayed degradation of the implant are partially incorporated by endogenous cells and/or are further degraded.

Another advantage of a layer created by means of a plasma chemical process is that the surface contaminants of the base material, which cannot be removed by the upstream treatment processes performed on the implant surface, are absorbed by the degradation-inhibiting intermediate layer and thus do not have any additional negative effect on the degradation process. Furthermore, segregations of the implant body, in some cases with sharp edges, protrude out of the surface (for example, undissolved alloy constituents, e.g., yttrium and its compounds) or residues of the previous processing of the implant body are covered by the surface treatment. This yields a further increase in hemocompatibility and biocompatibility.

Furthermore, the porous structure of the intermediate layer due to the process has a high plastic deformation capacity. For example, the microcracks formed in dilatation of a stent are stopped due to energy accumulation and/or dissipation in the pores neighboring the microcracks. Therefore, there is no delamination of the intermediate layer.

The above object is also achieved by a method of producing a degradation-inhibiting layer structure (or a degradation-inhibiting coating) on the surface of an implant body, said method comprising the following steps: a) preparing the implant body, and b) applying the first layer to at least a portion of the body surface, such that the first layer contains a hydrogen-binding material, preferably palladium.

Use of the inventive coating method for production of a first layer with a hydrogen-binding material is simple and inexpensive to produce an inventive implant having the advantages described above.

In a preferred exemplary embodiment, the first layer is applied by immersing the implant body in a solution, preferably containing palladium and an electrolyte, said electrolyte being, for example, an aqueous electrolyte containing a surfactant or an electrolyte containing a hydrocarbon. The use of an immersion process for applying the first layer is especially inexpensive because it consumes very little energy.

Coating with the desired layer thickness indicated above is achieved in an advantageous manner when the implant body remains in the solution for a period of approx. 10 seconds to approx. 30 seconds.

As an alternative to use of an immersion method, the first layer may also be applied by means of a galvanic treatment in an aqueous solution in which an electric voltage is applied to the implant body, whereby the aqueous solution preferably contains a water-soluble conductive salt, e.g., potassium dihydrogen phosphate, a complexing agent, e.g., citric acid, ethylenediaminetetraacetic acid and/or tartaric acid as well as a metal compound containing palladium, e.g. a compound from the group comprising palladium(II) acetate trimer and tris(dibenzylideneacetone) dipalladium(0).

In particular after applying a plasma-chemically produced intermediate layer, it is advantageous for a first layer to be applied by means of a galvanic method, because after applying the intermediate layer, only one or more rinsing operations in distilled water need be performed. Coating in the electrolyte containing palladium is then performed according to the cathodic principle, which means that the Mg substrate, already coated by a plasma chemical method, is connected as the cathode. The anode is, for example, a revolving platinum-plated titanium sheet. The coating is performed in the low-voltage range using a d.c. voltage or pulsed d.c. voltage of max. 40 V.

In this method, it is also advantageous that the positively charged palladium ions are deposited in the zones of the greatest electric field density of the magnesium component during application of the first layer. In the presence of a plasma-chemically applied intermediate layer, these zones are the pores formed in this coating process. The palladium ions at the base of the pores and on the side walls are reduced to metallic palladium. There is no direct metallic contact between the material of the implant body and the magnesium or magnesium alloy because the base of the pores has a barrier layer up to 1 µm thick, comprising a mixture of oxides, hydroxides and phosphates. In another preferred exemplary embodiment, after subsequent rinsing in a suitable solvent, a final immersion process may be performed in a strongly alkaline medium (e.g., 25% ammonia solution or 2 to 4 molar sodium hydroxide solution), leading to constriction at the necks of the pores and thus to improved anchoring of the palladium at the base of the pore and on the walls of the pore.

As already explained, before applying the first layer, preferably at least a portion of the body surface is subjected to a plasma chemical treatment in an aqueous solution to create an intermediate layer; in this treatment, an electric voltage that creates the plasma is applied to the implant body. The aqueous solution here preferably has one or more ionic species selected from the group of phosphate ions, potassium ions and calcium ions to create the intermediate layer.

The intermediate layer preferably contains at least one compound selected from the group of phosphates, hydroxides and oxides of the biodegradable material.

As already described above, the intermediate layer contains pores such that a first layer of a hydrogen-binding material, preferably palladium, is formed preferentially at the base of the pores and on the side walls of the pores after the first layer has been applied, preferably by means of a galvanic treatment.

To achieve advantageous protection of the first layer as described above, in one exemplary embodiment, a second layer, preferably containing parylene and/or magnesium stearate, is applied to the first layer.

The statement of object above is also achieved by an implant obtainable by the inventive method described above. These inventive implants have the advantages indicated above in conjunction with the inventive production process.

EXAMPLES

The inventive method is explained below on the basis of examples in which all the features described constitute the subject of the invention, regardless of how they are combined in the claims or in the references back to previous claims.

Example 1

Production of an Implant with a Plasma-Chemically Produced Phosphate Layer with a Cathodic Aftertreatment in an Electrolyte Containing Palladium The body of an implant, preferably an endovascular stent, is first produced with the help of known technologies such as laser cutting, subsequent deburring and electropolishing.

Then anodic contact is established in an aqueous electrolyte containing potassium ions, calcium ions and phosphorus ions with the following composition to form the plasma chemical coating:
  65 ml/L ethylenediamine solution (99%),
  80 g/L potassium dihydrogen phosphate and/or 50 g/L calcium carbonate, or calcium citrate or calcium citrate malate,
  20 ml/L aqueous ammonium hydroxide solution (25%)
  25 g/L sodium carbonate.

Pulsed voltages between 250 V and 500 V (constantly rising voltage), current densities between 0.5 and 5 A/dm$^2$ and pulse frequencies between 100 Hz and 10 kHz are selected. The anticathode is made of stainless steel 1.4301. The plasma chemical reaction begins with a steady increase in bath voltage, leading to process-related porous surfaces. The pores have diameters between 0.1 µm and 8 µm. A surface layer and intermediate layer containing oxides, hydroxides and phosphates and also containing elements and compounds of the material of the implant body is formed as the reaction product of the plasma chemical reaction. In conclusion, a two-stage rinsing is performed in a suitable solvent.

Immediately thereafter, the stent, which is still in contact with a titanium or aluminum wire, is immersed in another inventive electrolyte solution of a defined electric conductivity. The electrolyte solution also contains metal compounds in addition to the water-soluble conductive salt (e.g., potassium dihydrogen phosphate) and complexing agents, e.g., citric acid, ethylenediaminetetraacetic acid, tartaric acid and metal compounds such as palladium(II) acetate trimer [Pd$(O_2CCH_3)_2]_3$ or tris(dibenzylideneacetone)dipalladium(0) [$(C_{17}H_{14}O)Pd_2]_3$. Before the subsequent coating operation, the magnesium component is then connected as the cathode and a constant or pulsed bath voltage amounting to max. 40 V is applied. During the galvanic process, palladium ions are deposited in the zones of the greatest electric field density of the magnesium component. These are the pores formed from the preceding coating operation. The palladium ions are reduced to metallic palladium at the base of the pores and on the walls of the pores. There is no direct metal contact with the magnesium base material because the base of the pores has a barrier layer up to 1 µm thick, consisting of oxides, hydroxides and phosphates. After the end of the process, the stent is rinsed several times in suitable solvents. A concluding immersion process in a strongly alkaline medium (e.g., aqueous 25% ammonia solution or 2 to 4 molar sodium hydroxide solution) leads to a narrowing of the necks of the pores and thus to better anchoring of the palladium on the base of the pores and on the walls of the pores.

Example 2

Production of an Implant with a Plasma Chemically Created Phosphate Layer with a Currentless Aftertreatment in a Colloidal Electrolyte Containing Palladium First, the implant body is manufactured as described in Example 1 and the plasma chemical coating of the implant body is performed according to Example 1 and finished with the two-stage rinsing. Next, instead of the galvanic coating described in Example 1, a currentless aftertreatment is performed in a colloidal palladium solution (30 mg/L to 5 g/L Pd) over a period of approx. 0.5 minutes to approx. 10 minutes. The solution may also contain tin(II) salts as colloid stabilizers.

Example 3

Production of an Implant with a Plasma-Chemically Produced Phosphate Layer with a Currentless Aftertreatment in an Electrolyte Containing Palladium with a Final Treatment (Immersion in Magnesium Stearate)

First, the method according to Example 2 is performed (including the procedure according to Example 1). Then the implant body is suspended from a plastic string (e.g., polyamide) and next immersed in a solution to apply the magnesium stearate. The solution consists, for example, of nine parts high-purity acetone, isopropanol or tetrahydrofuran and one part magnesium stearate (parts based on the weight of the respective components). The immersion process is performed at temperatures between room temperature and the respective boiling point of the solvent (e.g., 56° C. in the case of acetone, 82° C. in the case of isopropanol and 64° C. with tetrahydrofuran). These temperatures are lower when the immersion process is performed in an evacuable desiccator in which a vacuum of approx. 100 mbar is created by means of a pump. The filigree surface structures and the microporous surface structures and undercuts formed by the preceding plasma chemical pretreatment and/or structures having a complex shape are effectively freed of residual gas in this way. Complete coverage of the implant surface by the magnesium stearate, which also penetrates into the surface structures and undercuts, can be accomplished in the solution in this way. After a dwell time of approx. 3 minutes in the immersion bath, the desiccator is aerated, the implant is removed from the immersion bath and then dried at a temperature of 60° C. in a circulating air cabinet, while still suspended from the plastic string. The layer thickness of the resulting magnesium stearate coating is in the range of approx. 0.5 µm to approx. 10 µm.

Due to the vacuum prevailing in the desiccator, the magnesium stearate is deposited very uniformly on the surface of the implant body. A low drying temperature results in a gradual release/evaporation of the solvent of the immersion solution in an advantageous manner, thus yielding a pore-free magnesium stearate layer. If the implant produced in this way is a stent, then the body provided with the first layer and the intermediate layer can then be completed with a catheter and subjected to radiation sterilization.

Example 4

Production of an Implant by Means of Surface Treatments According to Examples 2 or 3 without Prior Plasma Chemical Treatment The methods explained above on the basis of Examples 2 or 3 may also be performed even without a prior plasma chemical treatment, starting from the implant body produced by laser cutting and then deburring and electropolishing.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

Example 5

Production of an Implant by Means of an Immersion Process

Another possibility of surface loading with palladium consists of using an immersion process in which nanoscale (and/or microscale) palladium is stirred into an aqueous electrolyte containing a surfactant or hydrocarbon. The particular diameter may vary between 20 nanometers and 15 micrometers. The surfactant component contributes toward reducing the surface tension of the nanoscale palladium. The resulting emulsion keeps the palladium particles in suspension. The magnesium implant body previously plasma-chemically coated in the electrolyte solution (see Example 1) is currentlessly immersed into the mixture, which is slightly cloudy to opaque, depending on the concentration of the palladium powder. The solution is agitated by means of a magnetic stirrer, so there are no concentration differences among the palladium particles in the coating container. The stent remains in the solution for 30 seconds to 10 minutes, then is pulled out and immediately placed in a drying oven. After drying, there remains a layer several micrometers thick containing nanoscale palladium particles on the stent.

To prevent this layer from flaking off in subsequent assembly operations, the magnesium implant is subjected to a final immersion treatment in a solution containing magnesium stearate to produce the second layer. Then the component is either packaged and/or (in the case of stents) mounted on the catheter.

Alternatively, an uncoated (only electropolished) magnesium implant body may be immersed in the palladium solution indicated above.

Example 6

Applying the Second Layer Containing Parylene

First the implant is produced according to one of the methods described in Examples 1 to 5. Then a parylene C layer or parylene N layer approx. 0.5 µm to approx. 7 µm thick is applied by means of a CVD process (instead of the magnesium stearate coating in Example 5).

The stents to be treated are then placed in a coating chamber. The coating operation is begun with a weight (e.g., approx. 4 g for a desired layer thickness of 1 µm and approx. 10 g for a layer thickness of 3 µm) which takes into account the chamber volume and the stent surface area. The vaporizer temperature is between 100° C. and 170° C. The powdered monomer is drawn over a hot plate because of the applied chamber vacuum of approx. 0.5 Pa to 50 Pa. The temperature of the hot plate is between 650° C. and 730° C. After a coating time of approx. 1 hour (for a desired layer thickness of 1 µm) or 3 hours (for a desired layer thickness of 3 µm), the implants have a homogeneous coating of parylene C (or N).

Example 7

Producing a Porous Implant by Means of an Immersion Process

A foamed, open-pored magnesium implant body is immersed in a solution containing palladium particles in vacuo. The pores are infiltrated with the suspension. Subsequent regulated heating at temperatures between approx. 100° C. and approx. 250° C. leads to vaporization of the solvent. The palladium particles remain in the pore structure.

This may be followed by subsequent sealing in a solution containing magnesium stearate in a vacuum. This causes greater adhesion of the palladium particles in the pore structure. A final hot storage at temperatures between 80° C. and 150° C. leads to extensive closure of the pores and reduces the actual component surface coming in contact with the body.

In another preferred exemplary embodiment, the implant body is treated electrochemically, preferably being electrochemically polished before the plasma chemical treatment to produce the intermediate layer or the first layer. In this process, impurities on the surface of the implant body are removed, so that the plasma chemical treatment is performed on a defined surface.

The plasma chemical treatment of the implant body is preferably performed to create the intermediate layer by applying a pulsed positive voltage to the body, its amplitude exceeding at least approx. 90 V during most of the treatment, especially preferably at least approx. 100 V, and preferably rising in the course of the treatment. Due to these high pulsed voltages with a pulse period of preferably max. 20 microseconds, especially preferably approx. 5 microseconds, plasmas are generated at the surface of the implant body, lasting for a few microseconds and leading to reaction of the metallic material of the implant body with the electrolyte. Between the voltage pulses, there is a resting phase of preferably approx. 100 microseconds. The plasma chemical process is preferably performed with a current density of at least approx. 5 mA/cm$^2$, preferably at least approx. 10 mA/cm$^2$.

Implants produced by means of the method described here will degrade within the desired time windows. Surprisingly, the degradation can be controlled by a layer (intermediate layer) which is designed to be porous.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implant formed as an endovascular stent, having a body forming most of the mechanical integrity of the implant, the body comprising at least one at least largely biodegradable metallic material, optionally magnesium or a magnesium alloy, characterized in that the implant has a first layer comprising a hydrogen-binding material comprising palladium on at least a portion of the body surface; a second layer comprising parylene and/or magnesium stearate arranged over and contacting the first layer on at least a portion of the surface of the implant body, wherein the palladium comprises palladium particles having grain sizes between approximately 20 nm and approximately 15 µm.

2. The implant according to claim 1, characterized in that the first layer has a layer thickness of approximately 1 µm to approximately 10 µm, optionally approximately 2 µm to approximately 6 µm.

3. The implant according to claim 1, characterized in that the palladium forms palladium hydride to act as a sacrificial element during degradation of the implant, further wherein the grain sizes are between approximately 50 nm and approximately 500 nm.

4. The implant according to claim 1, characterized in that the second layer has a layer thickness of approximately 0.5 µm to approximately 10 µm.

5. An implant formed as an endovascular stent, having a body forming most of the mechanical integrity of the implant, the body comprising at least one at least largely biodegradable metallic material, optionally magnesium or a magnesium alloy, characterized in that the implant has a first layer comprising a hydrogen-binding material comprising palladium on at least a portion of its the body surface; a second layer comprising parylene and/or magnesium stearate arranged over and contacting the first layer on at least a portion of the surface of the implant body; and an intermediate layer that is a product of a plasma chemical treatment of the body's biodegradable metallic material and arranged between the surface of the body and the first layer, the intermediate layer being porous and being provided over at least a portion of the body surface of the implant, the thickness of the intermediate layer being approximately 1 µm to approximately 20 µm, optionally approximately 2 µm to approximately 8 µm.

6. The implant according to claim 5, characterized in that the plasma chemical treatment forms the intermediate layer with at least one compound selected from the group comprising consisting of phosphates, hydroxides, and oxides of the biodegradable metallic material.

7. The implant according to claim 1, wherein the second layer comprises magnesium stearate.

8. The implant according to claim 6, wherein the pores comprise bases with sidewalls, further wherein the first layer forms at the bases and the sidewalls of the pores.

9. The implant according to claim 1, further comprising a porous intermediate layer arranged between the surface of the body and the first layer, wherein the intermediate layer comprises at least one member selected from the group consisting of phosphates, hydroxides and oxides of the biodegradable metallic material, further wherein the intermediate layer is a product of plasma chemical treatment of the body.

10. The implant according to claim 5, wherein the second layer comprises magnesium stearate.

\* \* \* \* \*